(12) United States Patent
Yamamoto et al.

(10) Patent No.: US 7,427,395 B2
(45) Date of Patent: Sep. 23, 2008

(54) CHEMOTHERAPEUTIC AGENT-INCORPORATED PHARMACEUTICAL PREPARATION

(75) Inventors: Seiji Yamamoto, Suita (JP); Hitoshi Kotani, Ikeda (JP); Yasufumi Kaneda, Minoh (JP)

(73) Assignees: Genomidea Inc., Osaka (JP); Anges MG, Inc., Osaka (JP)

( * ) Notice: Subject to any disclaimer, the term of this patent is extended or adjusted under 35 U.S.C. 154(b) by 385 days.

(21) Appl. No.: 10/530,473

(22) PCT Filed: Oct. 29, 2003

(86) PCT No.: PCT/JP03/13860

§ 371 (c)(1), (2), (4) Date: Apr. 6, 2005

(87) PCT Pub. No.: WO2004/039406

PCT Pub. Date: May 13, 2004

(65) Prior Publication Data

US 2006/0165656 A1  Jul. 27, 2006

(30) Foreign Application Priority Data

Nov. 1, 2002  (JP)  ............................ 2002-320577

(51) Int. Cl.
*A61K 48/00* (2006.01)

(52) U.S. Cl. .................... 424/93.2; 424/450; 435/235.1

(58) Field of Classification Search ........................ None
See application file for complete search history.

(56) References Cited

U.S. PATENT DOCUMENTS

| | | | |
|---|---|---|---|
| 5,077,056 A * | 12/1991 | Bally et al. | ................. 424/450 |
| 2003/0013195 A1 | 1/2003 | Kaneda | |
| 2003/0038730 A1 | 2/2003 | Imafuku et al. | |
| 2003/0172136 A1 | 9/2003 | Katagawa et al. | |
| 2004/0253272 A1 | 12/2004 | Kaneda | |

FOREIGN PATENT DOCUMENTS

| | | |
|---|---|---|
| EP | 1170363 A1 | 1/2002 |
| EP | 1416759 | 5/2004 |
| EP | 1416760 | 5/2004 |
| JP | 2001/145140 | 5/2001 |
| JP | 2001-286282 A | 10/2001 |
| JP | 2002-65278 | 3/2002 |
| JP | 2002-065278 A | 3/2002 |
| JP | 2003-52082 | 2/2003 |
| JP | 2003-52093 | 2/2003 |
| JP | 3445986 | 6/2003 |
| WO | 97/04748 A1 | 2/1997 |
| WO | WO 97/04748 | 2/1997 |
| WO | 01/57201 A1 | 8/2001 |
| WO | WO 01/57204 A1 | 8/2001 |
| WO | 03/14338 A1 | 2/2003 |
| WO | WO 03/014338 A1 | 2/2003 |

OTHER PUBLICATIONS

Kumar et al., FEBS Letters, vol. 391, 1996, pp. 17-20.*
English Language Abstract of JP 2001/145140. (2001).
English Language Abstract of JP 2003-52093. (2003).
English Language Abstract of JP 2003-52082. (2003).
Howell et al. "Clinical applications of a novel sustained-release injectable drug delivery system: DepoFoam technology" Cancer J. 7:219-227 (2001).
Kaneda et al., "Hemagglutinating virus of Japan (HVG) envelope vector as a versatile gene delivery system" Mol. Ther. 6: 219-226 (2002).
Kaneda, "Virosomes, evolution of the liposome as a targeted drug delivery system" Adv. Drugs Delivery Rev. 43:197-205 (2000).
Tanaka et al., "NEW Yakurigaku" pp. 557-566 (1997) and summary in English.
International Search Report of PCT/JP03/13860 (2004).
Y. Kaneda et al., "Hemagglutinating Virus of Japan (HVG) Envelope Vector as a Versatile Gene Delivery System", Moelcular Therapy, Aug. 2002, vol. 6, No. 2, pp. 219-226.
Y. Kaneda, "Virosomes, evolution of the liposome as a targeted drug delivety system", Advanced Drug Delivery Reviews, 2000, vol. 43, pp. 197-205.
C. Tanaka et al., "NEW Yakurigaku", Aug. 1, 1997, pp. 557-566.
International Search Report of PCT/JP03/13860 mailed Feb. 10, 2004.

* cited by examiner

*Primary Examiner*—James S Ketter
(74) *Attorney, Agent, or Firm*—Nixon & Vanderhye P.C.

(57) ABSTRACT

An apparatus and a method of remote control which can enable real time operation of a device in home from a terminal device at remote location through a network are provided. A first server communicates with a terminal device through the Internet and generates device control data for controlling the device. A second server communicates with the device in a predetermined manner to acquire and store a specific address of the device, generates transmission data for transmission of the received device control data from the first server to the device based on the specific address, and transmits the transmission data to the device. This allows real time control of the device from the terminal device through the network to be realized.

23 Claims, 3 Drawing Sheets

CHEMOTHERAPEUTIC AGENT-INCORPORATED PHARMACEUTICAL PREPARATION

This application is the US national phase of international application PCT/JP2003/013860 filed 29, Oct. 2003, which designated the U.S. and claims priority of JP 2002-320577, filed 1, Nov. 2002, the entire contents of each of which are hereby incorporated by reference.

TECHNICAL FIELD

The present invention relates to a pharmaceutical preparation used in transfection of cells or living organisms with a chemotherapeutic agent by a gene delivery vector.

BACKGROUND ART

It is said that the cure rate in cancer treatment is about 50%. at present, and generally, such cure is brought about often by topical therapy such as surgical therapy and radiotherapy. It is in a very low rate that chemotherapy as systemic therapy can contribute solely to cue, particularly in treatment of solid tumor, and usually chemotherapy is used in combination with various therapies.

On the other hand, surgical therapy enables surgery in every organ cancer and is considered to reach completion as therapy, and no further improvement in cure rate can be expected. The treatment results of susceptible organ cancers by radiotherapy also arrive at an almost fixed rate, and no further improvement in cure rate can be expected as well.

Accordingly, no significant improvement in cancer cure rate by these therapies can be expected in the future, and the development of further excellent chemotherapy is essential for further improving the cancer cure rate of 50% at present to arrive at cure for cancer.

An purpose of an anticancer agent used in chemotherapy lies in cytocidal effect on cells having a high ability to grow, such as cancer cells, and its damage to normal cells particularly myeloid cells having a high cellular growth ability is significant, and as a result, severe pain is given to patients. This is because the transfer of the anticancer agent is due to systemic administration by an injection, and the anticancer agent reaches normal cells other than cancer cells, so that the normal cells are killed and homeostasis does not function.

At present, however, the effect of an anticancer agent administered alone is regarded to be approximately about 30%, and it is expected that genetic information analysis and study on genome proceed so that selection of a suitable anticancer agent feasible can be expected in the future, but it is said that the therapy with the anticancer agent at present results in higher side effects.

This is because normal cells are damaged by systemic administration of an anticancer agent. Accordingly, if cancer tissue-specific delivery of the anticancer agent and subsequent incorporation thereof into cancer cells can be established, an ideal system of delivering the anticancer agent can be realized. In addition, if incorporation of the anticancer agent into a vesicle is feasible, a therapeutic method that is specific for target organ and cell with less influence (side effect) on normal cells can be established. Further, this can lead to reassessment of anticancer agents whose development was abandoned because of their strong side effects.

DISCLOSURE OF THE INVENTION

As a result of extensive study for solving the problem described above, the present inventors could complete a pharmaceutical preparation comprising, as an active ingredient, a virus envelope vector having a chemotherapeutic agent incorporated therein.

Accordingly, the present invention provides, for example, a pharmaceutical preparation comprising an anticancer agent or the like incorporated in e.g. an inactivated HVJ-E vector having an ability to incorporate a foreign gene.

The present invention relates to a pharmaceutical preparation used in transfection of cells or living organisms with a chemotherapeutic agent, preferably a cancerocidal agent, an anticancer agent, or an antitumor agent (hereinafter referred to collectively as anticancer agent), by using a gene delivery vector. The present invention relates more specifically to a pharmaceutical preparation by which a highly toxic anticancer agent is transferred by a gene delivery vector to the living organism and allowed to reach a target organ or cell safely with a reduction in side effects.

BEST MODE FOR CARRYING OUT THE INVENTION

Hereinafter, the present invention is described in more detail.

The chemotherapeutic agent used in the present invention is not particularly limited insofar as it is a low-molecular compound acting directly on cells, and for example, "Seikagaku Jiten" (Dictionary of Biochemistry), third edition, published by Tokyo Kagaku Dojin, describes: "At present, the subject of chemotherapy, that is, therapy using chemical substances of highly selective toxicity, has spread not only to microbial infections but also to malignant tumors", and it goes without saying that antibacterial agents, antitumor agents etc. are contained in the chemotherapeutic agent.

Preferable examples of the chemotherapeutic agent in the present invention include a cancerocidal agent, an anticancer agent or an antitumor agent (hereinafter referred to collectively as anticancer agent), and specifically the anticancer agent includes bleomycin and derivatives thereof, anthraquinone-based cancerocidal agents including adriamycin and daunomycin, mitomycin and derivatives thereof, actinomycin and derivatives thereof, taxane derivatives such as taxol, camptothecin and derivatives thereof such as irinotecan, cisplatin and derivatives thereof, staurosporine and derivatives thereof, vincristine, streptozotocin, 5-fluorouracil (5-FU) and derivatives thereof, viralbicin and dolastatin, as well as pharmacologically acceptable salts thereof.

Preferable among these chemotherapeutic agents are bleomycin and derivatives thereof, and specific examples include bleomycin or pharmacologically acceptable salts thereof, or peplomycin or pharmacologically acceptable salts, more specifically bleomycin hydrochloride, bleomycin sulfate and peplomycin sulfate.

When the pharmaceutical preparation of the present invention is used as an anticancer agent, the type of cancer to which it is applicable is not particularly limited, and specifically, solid cancer, blood cell cancer, and the like can be exemplified. Among these cancers, the solid cancer is a preferable subject to which the pharmaceutical preparation is applicable.

Specific examples of the solid cancer include lung cancer, breast cancer, digestive organ cancer, head and neck cancer, gynecologic cancer, urologic cancer, soft tissue and bone sarcoma, malignant lymphoma, cancers of unknown primary etc., and more specifically, for digestive organ cancers, stomach cancer, colon cancer, and esophagus cancer are exemplified, for head and neck cancers, upper jaw cancer, tongue cancer, lip cancer, pharynx cancer, larynx cancer, and oral cavity cancer are exemplified, for gynecologic cancers, uterus cancer, ovarian cancer, and uterine cervical cancer are exemplified, and for urologic cancers, prostate cancer is exemplified.

Among these solid cancers, more preferable subjects include skin cancer, skin malignant tumor, head and neck cancers (upper jaw cancer, tongue cancer, lip cancer, pharynx cancer, oral cavity cancer, and the like), lung cancer (particularly primary and metastasis flat epithelial cancer), esophagus cancer, malignant lymphomas (reticulum sarcoma, lymphosarcoma, Hodgkin's disease, and the like), uterine cervical cancer, neuroglioma, thyroid cancer, and prostate cancer.

The virus envelope vector in the present invention is a virus envelope which is prepared by removing RNA or DNA from virus. It is usually utilized to incorporate a gene, polynucleotide, oligonucleotide, plasmid or the like thereinto, for transfection.

The type of the virus is not limited, and specifically the virus includes, for example, viruses belonging to a family selected from the group consisting of the retrovirus family, togavirus family, coronavirus family, flavivirus family, paramyxovirus family, orthomyxovirus family, bunyavirus family, rhabdovirus family, poxvirus family, herpes virus family, baculovirus family, and hepadna virus family.

Specifically, the virus in the present invention includes, for example, Sendai virus, retrovirus, adenovirus, adeno-associated virus, herpes virus, vaccinia virus, poxvirus, influenza virus, and the like.

Among these viruses, Sendai virus (hemagglutinating virus of Japan (referred to hereinafter as HVJ)) that is one of mouse pneumonia viruses can be mentioned as a preferable example.

Specifically, Sendai virus, for example, VR-105 and VR-907 can be purchased from American Type Culture Collection ((ATCC), telephone 1-703-365-2700, P.O. Box 1549, Manassas, Va. 20108, USA,
on the World Wide Web at atcc.org/SearchCatalogs/
longview.cfm?view=av,152 376,VR-105&text=Sendai&max=20,
on the World Wide Web at atcc.org/SearchCatalogs/
longview.cfm?view=av,137 5478,VR-907&text=Sendai&max=20).

The virus envelope vector is described in more detail in, for example, JP-A 2001-286282 (WO01/57204), JP-A 2002-065278, WO-A 03/014338 (PCT/JP02/07879), and can be prepared specifically according to e.g. Example 8 in JP-A 2001-286282.

In the step of incorporating a chemotherapeutic agent in the virus envelope vector, a surfactant is preferably used, and specific examples of the surfactant include Triton X100, deoxycholic acid or a salt thereof, and cholic acid or a salt thereof. Preferably, the salt of deoxycholic acid includes sodium deoxycholate, and preferably, the salt of cholic acid includes sodium cholate.

The form of the pharmaceutical preparation of the present invention is not limited, but its specific example is an injectable solution, ointment, or the like, preferably an injectable solution.

Here, the present inventable solution is described in more detail by reference to the inactivated Sendai virus envelope vector (referred to hereinafter as HVJ-E vector).

When an anticancer agent is incorporated into the HVJ-E vector, the anticancer agent is dissolved in a buffer solution. The buffer solution used herein is not limited, and specifically, for example, TE buffer solution (10 mM Tris, 1 mM EDTA (pH 8.0)), PBS (phosphate buffer solution) can be suitably selected and used wherein the pH of the buffer solution is preferably 6 to 9.

A preferable feature of the present invention is that, in an in vitro experiment, an anticancer agent having a strong side effect or toxicity can be incorporated into HVJ-E vector to be delivered directly into cells without leakage of the anticancer agent into a culture solution.

In an in vivo animal experiment, not systemic administration but local administration of the anticancer agent is feasible, and the anticancer agent can be efficiently delivered into solid-cancer cells only.

Humans can be treated by chemotherapy of administering the anticancer agent-incorporated HVJ-E vector solely, or by locally administering it into progressive cancer patients whom the anticancer agent cannot be administered, to attain cancer regression, and simultaneously using radiotherapy and/or surgical treatment to achieve further excellent anticancer effects.

In an in vitro experiment, host cells are transfected with the anticancer agent-incorporated HVJ-E vector. As the procedure in this case, for example, a method of adding a solution of the anticancer agent-incorporated HJV-E vector to a medium for culturing the cells can be used.

The transfection is performed for about 30 minutes to 48 hours when it is carried out at 37° C. Judgment of the effect is conducted preferably by counting the number of viable cells or by WST assay (technique of counting viable cells; cell counting kit, Dojin Kagaku).

When the subject of an in vivo animal experiment is, for example, a mouse, it is preferable that a normal mouse that is not an immune-deficient mouse is used where the cancer cell is an isograft, and that a nude mouse or SCID mouse is used in the case of xenograft.

Cancer cells cultured in a Petri dish are transplanted subcutaneously to a mouse, and after growth of the transplanted cells, the anticancer agent-incorporated HVJ-E vector is administered into the grown solid cancer, and the major axis and minor axis of the cancer can be measured to determine the anticancer effect.

According to the present invention, there is provided a method capable of delivering an anticancer agent having a strong side effect to the site of a cancer easily and safely.

Accordingly, the HVJ-E vector can be used to enable new chemotherapy for any solid cancer, which is increasing rapidly in Japan, such as lung cancer, breast cancer, digestive organ cancers such as stomach cancer, colon cancer or esophagus cancer, head and neck cancers (upper jaw cancer, tongue cancer, lip cancer, pharynx cancer, larynx cancer, oral cavity cancer etc.), gynecologic cancers (uterus cancer, ovarian cancer, uterine cervical cancer etc.), urologic cancers (prostate cancer), soft tissue and bone sarcoma, malignant lymphoma, cancers of unknown primary, and the like.

EXAMPLES

Hereinafter, the present invention is described in more detail by reference to Examples, but the present invention is not limited by these Examples.

Example 1

In vitro Experiment

According to Example 8 in JP-A 2001-286282, 6,000 HAU/600 μl (for six 6-well plates) of inactivated HVJ-E vector was allowed to have a change in temperature from −80° C. to 34.5° C. A microtube containing the sample was centrifuged at 15,000 rpm for 15 minutes at 4° C. to give the HVJ-E vector as a precipitate, and the supernatant was removed. The resulting precipitate was suspended in 60 μl bleomycin/PBS (5 mg/ml) (bleomycin HCl manufactured by Nippon Kayaku Co., Ltd.) solution. Further, 2 μl of 3% Triton-X100 was added thereto to prepare a sample containing Triton-X100 at a final concentration of 0.1%, which was then left on ice for 15 minutes. Thereafter, 500 μl PBS solution was added thereto. The microtube was centrifuged at 15,000 rpm for 15 minutes at 4° C., and the supernatant was removed without removing the precipitate, and 500 μl PBS solution was added again to the precipitate. The microtube was centrifuged again at 15,000 rpm for 15 minutes at 4° C., and the supernatant was removed without removing the precipitate.

The resulting precipitate was suspended in 180 μl PBS, and the resulting sample solution was pipetted in a volume of 30 μl/microtube into 6 microtubes. Five microlitters of protamine sulfate solution prepared at 5 mg/ml and 500 μl DMEM solution (Dulbecco's modified Eagle medium) were added to each tube.

As the administration group, the followings were prepared and compared to evaluate their effect.
HVJ-bleomycin group; 1,000 HAU, bleomycin 200 ng/DMEM 500 μl/well.
HVJ-PBS group: 1,000 HAU/DMEM 500 μl/well.
1/50 bleomycin group: bleomycin 50 μg/DMEM 500 μl/well.
1/500 bleomycin group: bleomycin 5 μg/DMEM 500 μl/well.
1/5,000 bleomycin group: bleomycin 500 ng/DMEM 500 μl/well.
Medium group: DMEM The above sample solution was added to mouse colon carcinoma cell CT26 prepared on a 6-well plate. The plate was kept for 30 minutes in an incubator at 37° C., and then the medium was exchanged with 500 μl medium (DMEM containing 10% FCS). The cells were incubated for 2 days in a $CO_2$ incubator at 37° C. Two days later, the number of viable cells was counted to evaluate the anticancer effect.

Figure 1:
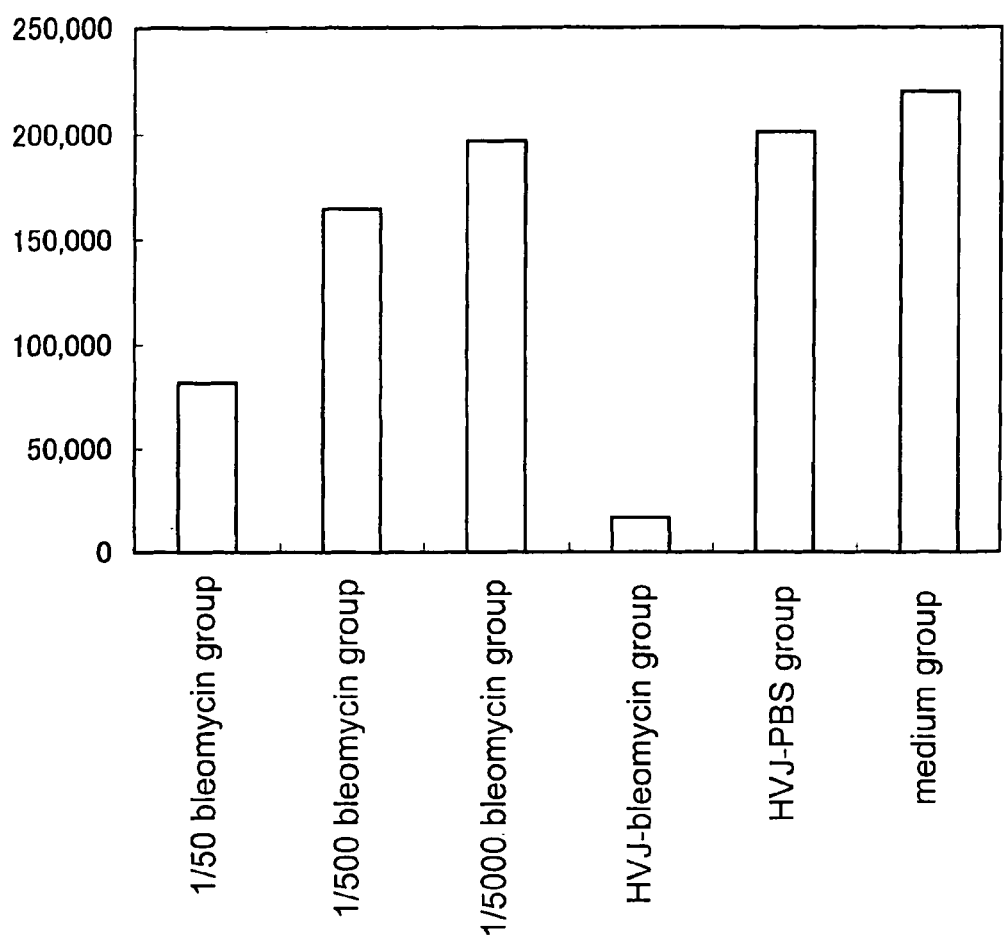
FIG. 1 is a graph wherein the numbers (mean±standard deviation) of viable cells in the respective groups in an in vitro experiment are compared.

The results are shown in the following Table and in FIG. 1.

TABLE 1

| Administration group | Number of mice | Mean | Standard deviation |
|---|---|---|---|
| 1/50 Bleomycin group | 2 | 81800 | 16688 |
| 1/500 Bleomycin group | 2 | 164600 | 13859 |
| 1/5,000 Bleomycin group | 2 | 196800 | 15274 |
| HVJ-bleomycin group | 2 | 16800 | 170 |
| HVJ-PBS group | 2 | 201100 | 8627 |
| Medium group | 2 | 220100 | 23617 |

The numbers of viable cells on average in the medium group and HVJ-PBS group were 220,100 and 201,100 respectively. The numbers of viable cells in the groups given bleomycin added to the medium (500 ng, 5 μg, 50 μg) were 196,800, 164,600 and 81,800 respectively, while the number of viable cells in the bleomycin HVJ-E incorporation group was 16,800. In percentage relative to the medium group (=100%), the degree of viable cells in the HVJ-PBS group was 91.4%, and the degrees of viable cells in the groups given bleomycin (500 ng, 5 μg and 50 μg) were 89.4%, 74.8% and 33.9% respectively, while the degree of viable cells in the bleomycin HVJ-E incorporation group was as low as 7.6%.

As a result, the dramatic cytocidal effect could be achieved successfully by incorporation of bleomycin into HVJ-E. The significant effect of bleomycin introduced directly by the HVJ-E vector into cells can be understood when it is taken into consideration that the cytocidal effect of bleomycin added to the culture solution is not so high.

This result indicated that by incorporating, into HVJ-E vector, the anticancer agent causing a severe side effect upon systemic administration, the chemical can be delivered directly to affected cells of the patient.

Example 2

In vivo Experiment

HVJ-E vector (6,000 HAU/600 μl) was rapidly dissolved by shifting the temperature from −80° C. to 34.5° C. A microtube containing the sample was centrifuged at 15,000 rpm for 15 minutes at 4° C. to give the HVJ-E vector as a precipitate, and the supernatant was removed. The resulting precipitate was suspended in 60 μl bleomycin/PBS (40 mg/ml) solution. Further, 2 μl of 3% Triton-X100 was added thereto to the final concentration of 0.1%, which was then kept on ice for 15 minutes. Thereafter, 500 μl PBS solution was added thereto. The microtube was centrifuged at 15,000 rpm for 15 minutes at 4° C., and the supernatant was removed without removing the precipitate, and 500 μl PBS solution was added thereto. The microtube was centrifuged again at 15,000 rpm for 15 minutes at 4° C., and the supernatant was removed without removing the precipitate. The resulting precipitate was suspended in 120 μl PBS.

The following administration groups were prepared and were compared to evaluate their effect.
HVJ-bleomycin administration group: 5,000 HAU, bleomycin 6.5 μg/100 μl/mouse
HVJ-PBS administration group: 5,000 HAU/100 μl/mouse
65 μg/ml bleomycin administration group: bleomycin/PBS (65 μg/ml), 100 μl/mouse
PBS administration group: 100 μl PBS In this animal experiment, BALB/c mice (8-week-old, male) were used. The site in which the cancer cell colon carcinoma CT26 was transplanted was a subcutaneous region in the back of a mouse, and hair on the back was shaved for measuring the volume of the transplanted cancer cells. The CT-26 cells to be transplanted were suspended in DMEM medium containing 10% FCS, and 5×10⁶ cells (100 μl PBS/mouse) were transplanted in the back. The mice were anesthetized by intraperitoneal administration of 500 μl of 20-fold-diluted Nembutal injection. The volume of the transplanted cancer cells was estimated by calculation of major axis×minor axis×minor axis/2. When the diameter of the tumor reached 7 to 8 mm one week after transplantation, 100 μl of the sample prepared above was administered into the site of the cancer in the mouse. On Days 7, 10, 13, 16 and 19 (that is, 3-day intervals) after transplantation of the cancer cells, the tumor diameter was measured to evaluate the anticancer effect. The number of animals was 8 in each group.

The results are shown in the following table and in FIG. 2. (Upper, mean; lower, standard deviation)

TABLE 2

|  | Number of days after administration | | | |
|---|---|---|---|---|
|  | 7 | 10 | 13 | 16 |
| 65 mg/ml bleomycin | 158.4 | 413.70 | 754.7 | 1234.6 |
|  | 25.4 | 71.20 | 206.6 | 332.8 |
| HVJ-bleomycin | 136.2 | 285.70 | 456.7 | 676.1 |
|  | 16.2 | 77.60 | 116.4 | 209.2 |
| HVJ-PBS | 164.3 | 362.20 | 688.1 | 1083.1 |
|  | 23.8 | 73.70 | 143.7 | 243.8 |
| Medium (PBS) | 158.7 | 418.20 | 738.7 | 1277.7 |
|  | 33.3 | 62.50 | 97.9 | 162.7 |

Figure 3:
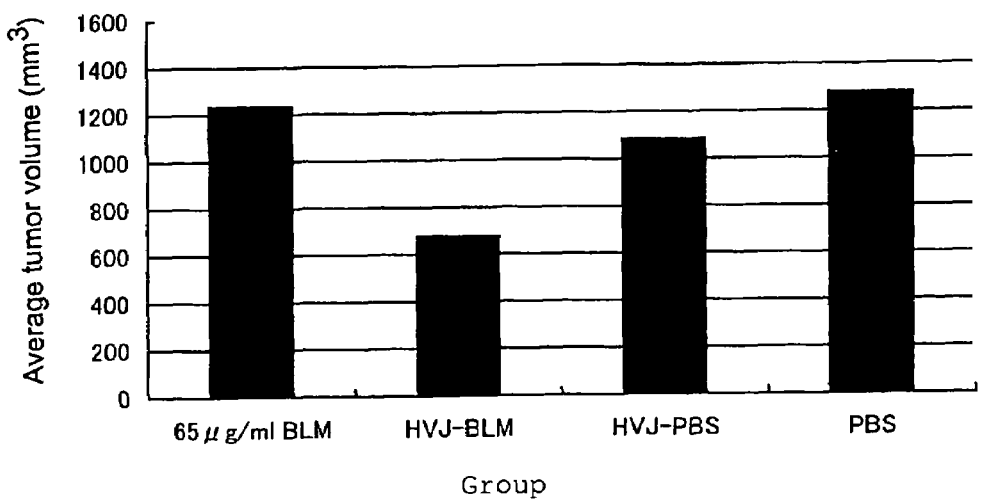
FIG. 3 is a graph showing a change in the average tumor volume (mean±standard deviation) in each group, relative to the medium (PBS) group, on Day 16 after administration in an in vivo experiment.

The average tumor volume in each group on Day 16 after administration, and the rate of change relative to the medium (PBS) group are shown in FIG. 3.

Figure 2:
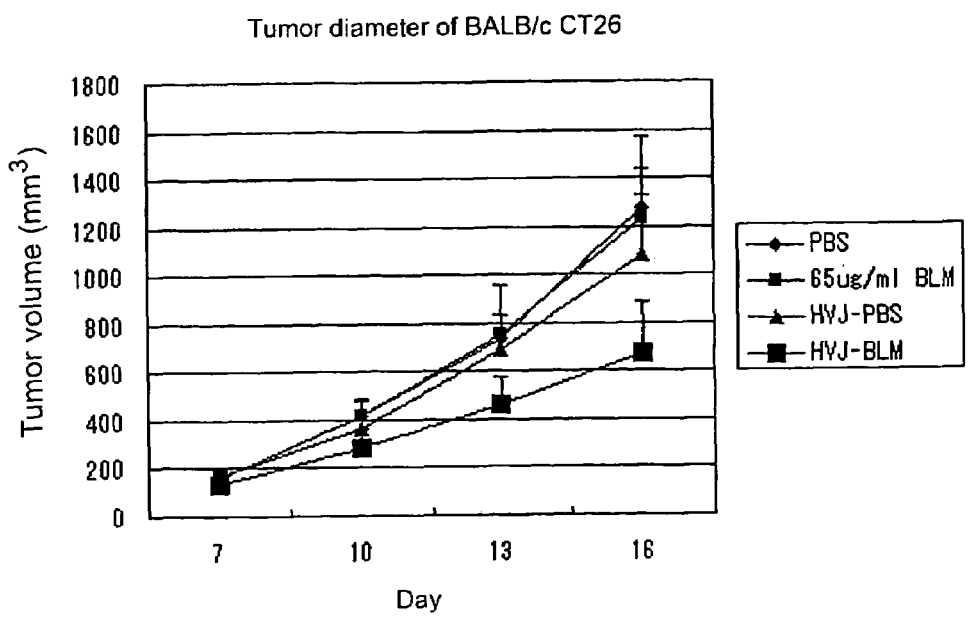
FIG. 2 is a graph wherein the average tumor volumes (mean±standard deviation) in the respective groups in an in vivo experiment are compared.

In the tumor diameter with no difference recognized at the time of inoculation with the prepared sample, a difference was recognized on and after Day 3 (corresponding to Day 10 in FIG. 2) after administration of the sample (FIG. 2). On Day 9 (corresponding to Day 16 in FIG. 2, that is, 9 days after administration of the sample), the volumes of the tumor, calculated by the equation above, were 1,277 mm3 in the PBS administration group, 1,235 mm³ in the 65 μg/ml BLM administration group, 1,083 mm³ in the HVJ-PBS administration group and 676 mm³ in the HVJ-BLM administration group respectively (FIG. 2). When expressed in percentage, the PBS administration group: 65 μg/ml BLM administration group: HVJ-PBS administration group: HVJ-BLM administration group=0%:3.4%:15.2%:47.1% (FIG. 3). In the group with bleomycin administered directly to the tumor-affected area, the tumor shrinkage effect was as low as 3.4% relative to the effect (0%) of the PBS administration group, and the shrinkage effect on tumor volume was hardly recognized. Whether this is due to the direct administration into the tumor as opposed to usually conducted systemic administration or due to administration at low concentration, or due to another factor, cannot be judged from the present results. The tumor volume shrinkage effect in the HVJ-PBS administration group was 15.2%, thus indicating that even the HVJ-E vector only attains a certain effect. This anticancer effect at a certain extent is possibly due to the immune action induced by HVJ-E. On the other hand, the tumor volume in the incorporated bleomycin administration group was 47.1%, indicating a high antitumor effect.

This Example has revealed:
Antitumor effect was hardly recognized in vivo by direct administration of bleomycin to the solid tumor cells.
Even the HVJ-E vector only was recognized to attain a weak antitumor effect.

When bleomycin is incorporated into HVJ-E and administered directly into the solid tumor, an excellent antitumor effect was recognized.

Example 3

In Vivo Experiment (2)

(1) Test Design

Mouse colon cancer-derived CT-26 cells were transplanted subcutaneously into the backs of 8-week-old BALB/cAnNCrj male mice, and 0.2 or 0.4 mg Platocin injection (cisplatin, CDDP)/body was once administered intraperitoneally into the animals (10 animals in each group) wherein the diameter of the tumor (major axis) reached about 5 mm, and on Day 1 after administration, HVJ-E, or HVJ-E/BLM containing 13.2 mg bleomycin, was administered once to the tumor. On Day 21 after administration into the tumor, the mice were sacrificed to examine the antitumor action of HVJ-E/BLM.

The constitution of the group in this test is shown below.

| Group | Intraperitoneal administration of the comparative control substance (mg/body)* | | Administration of the test substance into the tumor (mg/tumor)** | |
|---|---|---|---|---|
| Control group | Physiological saline | 0 | Physiological saline | 0 |
| HVJ-E group | Physiological saline | 0 | HVJ-E | 0 |
| 13 mg/tumor HVJ-E/BLM group | Physiological saline | 0 | HVJ-E/BLM | 13 |
| 0.2 mg/body CDDP group | CDDP | 0.2 | Physiological saline | 0 |
| 0.4 mg/body CDDP group | CDDP | 0.4 | Physiological saline | 0 |
| 0.2 mg/body CDDP-13 mg/tumor HVJ-E/BLM group | CDDP | 0.2 | HVJ-E/BLM | 13 |
| 0.4 mg/body CDDP-HVJ-E group | CDDP | 0.4 | HVJ-E | 0 |

*amount of cisplatin (CDDP)
**amount of bleomycin (BLM)

(2) Experimental Methods 2-1) Culture of Cancer Cells

Mouse colon cancer-derived CT-26 cells were cultured in DMEM medium containing 10% FBS at 37° C. in the presence of 5% $CO_2$.

The cells were cultured in a 75-cm² flask. The cells upon becoming about 80% confluent were subjected to subculture. After the DMEM (containing 10% FBS) was removed, the cells were washed with 10 mL phosphate-buffered physiological saline (PBS), and then the cells were released at 37° C. by adding 1 mL PBS containing 0.25% trypsin and 1 mmol/L EDTA-2Na. After 9 mL DMEM medium was added, the cells were collected and centrifuged (1000 rpm, 5 minutes), to recover the cells. After the supernatant was removed, the cells were diluted with DMEM medium containing 10% FBS and then cultured.

2-2) Preparation of a Suspension of the Cancer Cells

After the culture was removed from the cells which had became about 80% confluent, the culture flask was washed with PBS. A small amount of PBS containing 0.25% trypsin and 1 mmol/L EDTA-2Na was added and the flask was kept at 37° C. until release of the cells was initiated. The cells were collected with DMEM medium and centrifuged (1000 rpm, 5 minutes). After removal of the supernatant, the cells were suspended in PBS. The resulting suspension was centrifuged again (1000 rpm, 5 minutes). After the supernatant was removed, the residue was adjusted to $5 \times 10^7$ cells/ml with PBS.

2-3) Habituation of Mice

In the inspection and habituation period of 16 days, solid feed and drinking water were given freely.

2-4) Inoculation with the Cancer Cells

After the inspection and habituation were finished, hair of the animals was shaved by using hair clippers. Said cells (100 µL/site, $5 \times 10^6$ cells/body) were administered intracutaneously into the backs of 59 mice by using a disposal syringe and needle (26G). On the next day of administration, the cells were administered in the same manner into 57 animals (animals not administered).

2-5) Grouping of the Animals

The tumor diameter (major axis, minor axis) was measured on Days 4, 5, 6 and 7 after transplantation (measurement was not conducted after grouping). Animals with a tumor diameter (major axis) of 4.5 to 5.5 mm (actual measurement of 4.64 to 5.48 mm) were grouped by stratified randomization such that the average tumor diameter (major axis) became almost the same in each group.

2-6) Administration

Using a disposal syringe and needle, the control substance (1000 µL) was once administered intraperitoneally into each group, and 1 day later, the test substance (100 µL) was administered into the tumor.

2-7) Measurement of Tumor Diameter

The administration day was regarded as Day 0 after administration. On Days 3, 6, 9, 12, 15, 18 and 21 after administration, the tumor diameters in each mouse was measured and the tumor volume (major axis×minor axis×minor axis÷2) was calculated.

2-8) Measurement of Tumor Weight

All mice in each group (after fasting for 16 to 24 hours) on Day 21 after administration were subjected to euthanasia by exsanguination under anesthesia by intraperitoneal administration of an aqueous solution (6.48 mg/mL, 5 mL/kg) of pentobarbital sodium (Tokyo Kasei Kogyo Co., Ltd.), and then the tumor was excised and measured for its weight.

(3) Results 3-1) Tumor Volume

Figure 4:
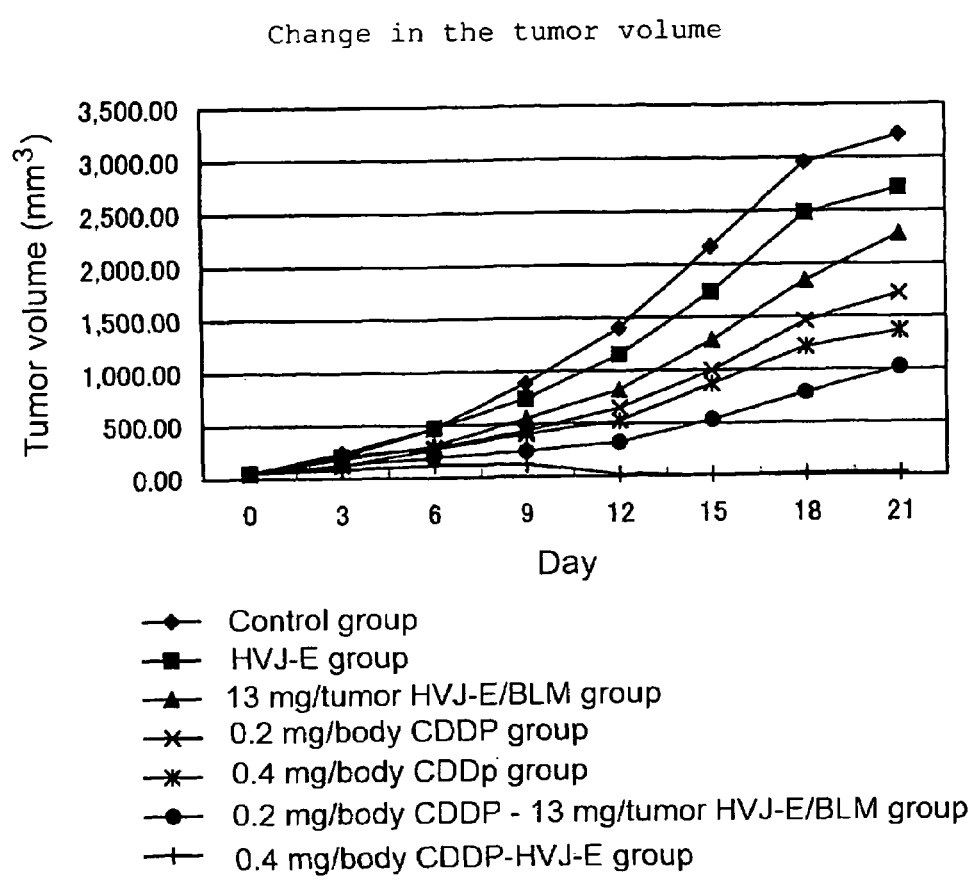
FIG. 4 is a graph showing the result of tumor volume in Example 3.

In the control group, HVJ-E group, 13 mg/tumor HVJ-E/BLM group, 0.2 mg/body CDDP group, 0.4 mg/body CDDP group and 0.2 mg/body CDDP-13 mg/tumor HVJ-E/BLM group, the tumor volume was increased with time until Day 21 after administration, and the average tumor volumes on Day 21 were 3216.14, 2716.00, 2283.84, 1720.14, 1367.62 and 1022.34 mm$^3$ respectively in the above groups (3 mice in the 0.4 mg/body CDDP group, and 10 mice in each of the other groups). In one surviving mouse in the 0.4 mg/body CDDP-HVJ-E group, the tumor volume on Day 6 after administration was increased to 122.27 mm$^3$, and the tumor volume was decreased to 118.82 mm$^3$ on Day 9 after administration, and further to 13.12-23.26 mm$^3$ on Day 12 to Day 21 after administration (see FIG. 4).

3-2) Tumor Weight

The tumor weights on Day 21 after administration were in the order of the control group (2570.35 mm)≧HVJ-E group (2428.64 mg)>13 mg/tumor HVJ-E/BLM group (1680.65 mg)≧0.2 mg/body CDDP group (1619.79 mg)>0.4 mg/body CDDP group (1164.13 mg)>0.2 mg/body CDDP-13 mg/tumor HVJ-E/BLM group (987.33 mg)>0.4 mg/body CDDP-HVJ-E group (90.4 mg). In the 0.2 mg/body CDDP-13 mg/tumor HVJ-E/BLM group, the tumor present at the time of administration disappeared in 2 out of 10 mice.

The foregoing results revealed that the 13 mg/tumor HVJ-E/BLM group shows an antitumor action on the CT-26 cells transplanted in mice, and its action is enhanced by combined use of intraperitoneal administration of CDDP.

The invention claimed is:

1. A pharmaceutical preparation comprising, as an active ingredient, a Sendai virus envelope vector having a chemotherapeutic agent incorporated therein.

2. The pharmaceutical preparation according to claim 1, wherein the chemotherapeutic agent is a cancerocidal agent, an anticancer agent, or an antitumor agent.

3. A pharmaceutical preparation comprising, as an active ingredient, a Sendai virus envelope vector having a chemotherapeutic agent incorporated therein; wherein the chemotherapeutic agent is at least one member selected from the group consisting of bleomycin and derivatives thereof, anthraquinone-based cancerocidal agents, mitomycin and derivatives thereof, actinomycin and derivatives thereof, taxane derivatives, camptothecin and derivatives thereof, cisplatin and derivatives thereof, staurosporine and derivatives thereof, vincristine, streptozotocin, 5-fluorouracil (5-FU) and derivatives thereof, viralbicin, dolastatin, and pharmacologically acceptable salts thereof.

4. The pharmaceutical preparation according to claim 3, wherein the chemotherapeutic agent is bleomycin or a pharmacologically acceptable salt thereof or peplomycin or a pharmacologically acceptable salt thereof.

5. The pharmaceutical preparation according to claim 3, wherein the chemotherapeutic agent is at least one member selected from the group consisting of bleomycin hydrochloride, bleomycin sulfate and peplomycin sulfate.

6. The pharmaceutical preparation according to claim 1, which is an injection.

7. A method of making a pharmaceutical preparation, which comprises: incorporating a chemotherapeutic agent into a Sendai virus envelope vector using a surfactant.

8. The method of making a pharmaceutical preparation according to claim 7, wherein the surfactant is one member selected from the group consisting of Triton X100, deoxycholic acid and salts thereof, and cholic acid and salts thereof.

9. A method of treating a solid cancer, which comprises:
administering to a patient a pharmaceutical preparation comprising, as an active ingredient. a Sendai virus envelope vector having a chemotherapeutic agent for the solid cancer incorporated therein.

10. The method of treating a solid cancer according to claim 9, wherein the solid tumor is one member selected from the group consisting of lung cancer, breast cancer, digestive organ cancer, head and neck cancer, gynecologic cancer, urologic cancers, soft tissue and bone sarcoma, malignant lymphoma and cancer of unknown primary.

11. The method of treating a solid cancer according to claim 9, wherein the solid tumor is one member selected from the group consisting of stomach cancer, colon cancer and esophagus cancer.

12. The method of treating a solid cancer according to claim 9, wherein the solid tumor is one member selected from the group consisting of upper jaw cancer, tongue cancer, lip cancer, pharynx cancer, larynx cancer and oral cavity cancer.

13. The method of treating a solid cancer according to claim 9, wherein the solid tumor one member selected from the group consisting of uterus cancer, ovarian cancer and uterine cervical cancer.

14. The method of treating a solid cancer according to claim 9, wherein the solid tumor prostate cancer.

15. A method of treating a cancer, which comprises using a chemotherapeutic agent-incorporated Sendai virus envelope vector in combination with a platinum complex and/or an antimetabolite.

16. The method of treating a cancer according to claim 15, wherein the platinum complex is one member selected from the group consisting of cisplatin, carboplatin, Parapratin and nedaplatin.

17. The method of treating a cancer according to claim 15, wherein the antimetabolite is one member selected from the group consisting of 6-mercaptopurine riboside, enocitabin, gemcitabine HOl, carmofur, cytarabine, cytarabine ocfosfate, tegafur, tegafur-uracil, tegafur-gimeracil-oteracil-potassium, doxifluridine, hydroxycarbamide, fluorouracil, methotrexate, mercaptopurine and fludarabine phosphate.

18. A method of treating a cancer, which comprises using a chemotherapeutic agent-incorporated Sendai virus envelope vector in combination with cisplatin and/or fluorouracil.

19. The method of treating a cancer according to claim 18, which comprises using a chemotherapeutic agent-incorporated Sendai virus envelope vector in combination with cisplatin and/or fluorouracil, and subsequent irradiation.

20. The method of treating a cancer according to claim 18, which comprises using a bleomycin or its pharmacologically acceptable salt-incorporated Sendai virus envelope vector in combination with cisplatin and/or fluorouracil, and subsequent irradiation.

21. The method of treating a solid cancer according to claim 9, wherein the pharmaceutical preparation is administered by an injection.

22. The method of treating a solid cancer according to claim 9, wherein the chemotherapeutic agent is at least one member selected from the group consisting of bleomycin and derivatives thereof, anthraquinone-based cancerocidal agents, mitomycin and derivatives thereof, actinomycin and derivatives thereof, taxane derivatives, camptothecin and derivatives thereof, cisplatin and derivatives thereof, staurosporine and derivatives thereof, vincristine, streptozotocin, 5-fluorouracil (5-FU) and derivatives thereof, viralbicin, dolastatin, and pharmacologically acceptable salts thereof.

23. The method of treating a solid cancer according to claim 9, wherein the chemotherapeutic agent is at least one member selected from the group consisting of bleomycin hydrochloride, bleomycin sulfate and peplomycin sulfate.

* * * * *